United States Patent
Zand

[11] Patent Number: 5,554,034
[45] Date of Patent: Sep. 10, 1996

[54] WORKPIECE ORGANIZER

[76] Inventor: Farnaz Zand, 212 E. Providencia, Burbank, Calif. 91502

[21] Appl. No.: 424,052

[22] Filed: Apr. 19, 1995

[51] Int. Cl.⁶ .............................. G09B 23/28; G09F 3/02
[52] U.S. Cl. .............. 434/263; 40/629; 40/913; 434/108; 434/238; 434/408
[58] Field of Search ................... 434/238, 236, 434/263, 270, 108, 408, 416; 40/628, 629, 913; 433/54

[56] References Cited

U.S. PATENT DOCUMENTS

| | | | |
|---|---|---|---|
| 1,984,839 | 12/1934 | Murray | 40/913 |
| 2,317,123 | 4/1943 | Warp | 40/629 |
| 2,414,614 | 1/1947 | Shurick, Sr. | 434/238 |
| 2,430,525 | 11/1947 | Miller | 40/629 |
| 2,863,603 | 12/1958 | Doupnik | 434/238 |
| 2,871,594 | 2/1959 | Halpert | 434/108 |
| 2,965,978 | 12/1960 | Olson | 434/108 |
| 3,782,009 | 1/1974 | Darnell | 434/238 |
| 4,841,653 | 6/1989 | Negley | 40/913 |
| 5,263,866 | 11/1993 | Campbell | 434/416 |
| 5,431,450 | 7/1993 | Coleman | 434/416 |

*Primary Examiner*—Paul J. Hirsch
*Attorney, Agent, or Firm*—Roger A. Marrs

[57] ABSTRACT

An organizer is disclosed herein for identifying a workpiece with a noted project or owner on a work chart. The chart has rows and columns containing indicia characterizing the workpiece and further including visual labels of a given shape and identification color. An identical set of labels is provided separate from the chart and having corresponding shape and color to those labels carried on the chart. A selected one of the separate labels is affixed to a particular workpiece so as to identify the workpiece with a particular row and column of indicia. A marking pen and an eraser is included to complete the organizer.

5 Claims, 1 Drawing Sheet

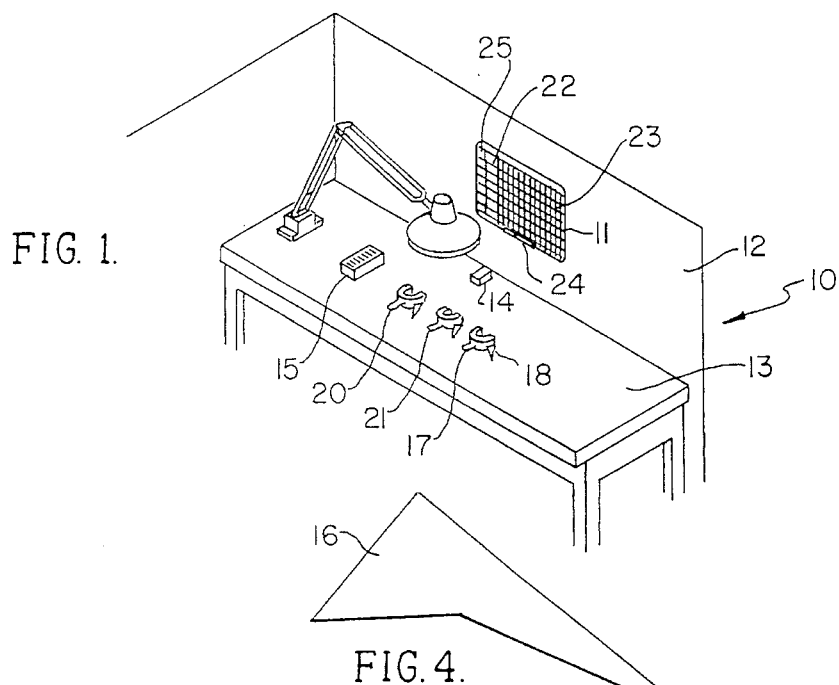
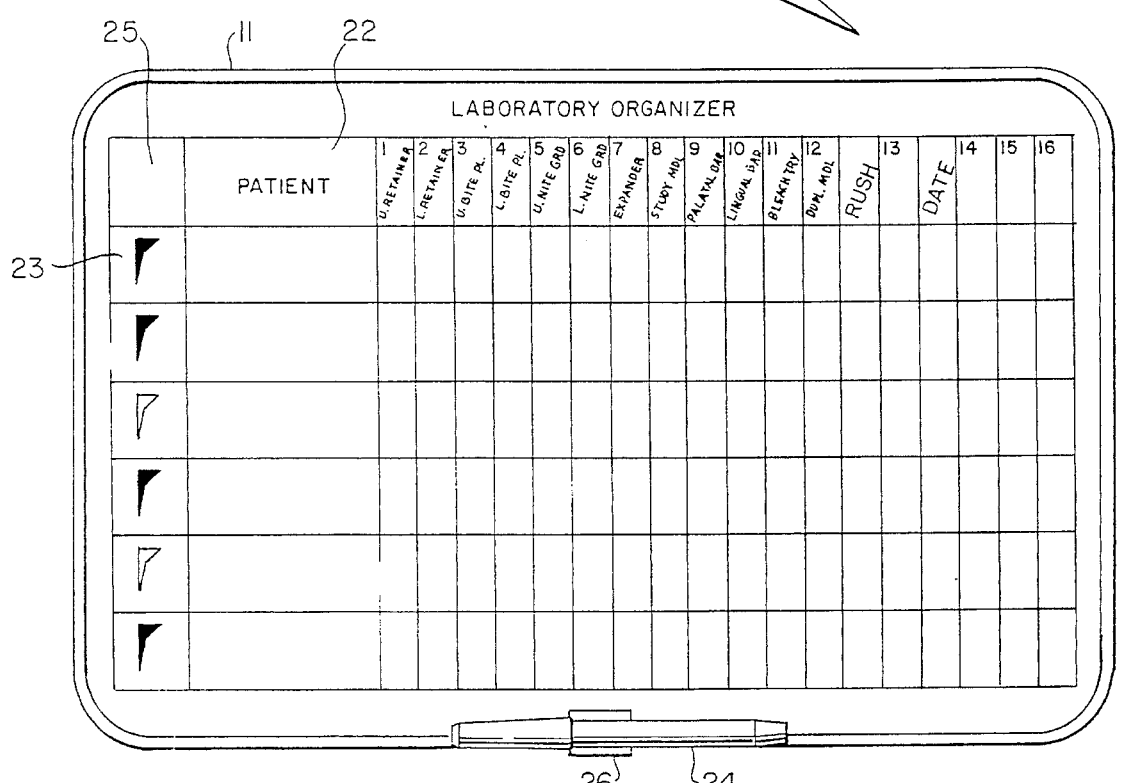
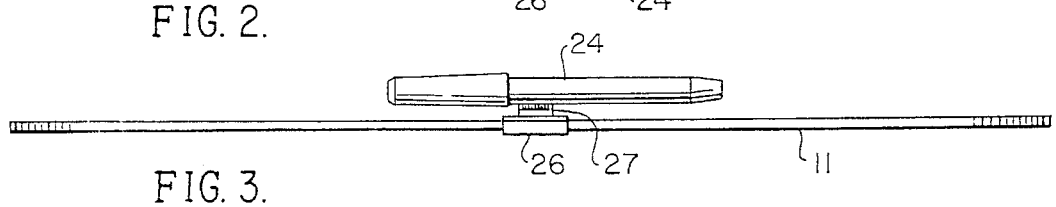

5,554,034

WORKPIECE ORGANIZER

BACKGROUND OF THE INVENTION

1. Field of the Invention

The present invention relates to the field of organizing systems whereby workpiece of work product identification can be allocated to particular owners or projects, and more particularly to a novel organizational device which includes a chart of information and sets of indicators whereby owner or project identity is maintained on the workpiece of work product through comparison of the identification indicators.

2. Brief Description of the Prior Art

Conventionally, it is the current practice to perform work or prepare a product for a particular individual in such a way that upon completion of the work, the product can be identified with the individual. More specifically, in the dental field, impression trays are used to take impressions from individuals and poured with plaster to make the mold from the teeth during the course of the day. The individual's fresh plaster mold is generally placed upon a work surface to dry and then transported to the laboratory. The wet plaster could not be marked and needs to be dry before the patient's name is written on the mold. Problems and difficulties have been encountered when employing such a conventional procedure, which stem largely from the fact that the unidentified wet mold may be mixed up or inadvertently placed out of order due to delayed marking so that upon return of the product, confusion results when trying to identify the product with a particular person. Since no identification is placed on the work product itself, the chance for confusion is greatly increased. Also, placing detailed information onto the work product itself is not possible at the time of pouring the impression since writing on wet plaster is not possible and has to be postponed until the mold is completely dry. Current procedures are time consuming and labor intensive and fail to solve the basic problem of avoiding confusion, misplacement and loss of the work product.

Therefore, a long-standing need has existed to provide an organizing system whereby a particular work product may readily be identified and subsequently associated with an owner or a project after remote work has been performed.

SUMMARY OF THE INVENTION

Accordingly, the above problems and difficulties are avoided by the present-invention which provides a novel organizing system which includes a board having a work surface laid out with a plurality of columns and rows across the surface thereof. Selected ones of the rows include indicia pertaining to work to be performed on a work product while a selected column is employed for carrying owner or product association with the work product intended to be worked upon. Another column in the plurality includes a key, code or graphic representation associated with each of the owner or product indicia carried in the column. The graphic representations represent a first set of indicators while a second set of indicators is provided which is separate and individual from the first set. The first and second sets of indicators are arranged in identical pairs so that the separate indicator of the second set may be placed on a workpiece or work product and be identified with its corresponding indicator of the first set carried on the column adjacent to an associated owner or product. The indicators of the second set are adapted for being physically incorporated into the workpiece of work product so that no need is required for adhesive, tape or other extraneous fastening materials or devices.

Additionally, the organizing system may further include a marking pen or pencil and an eraser so that the indicia may be changed at the desire of the user.

Therefore, it is among the primary objects of the present invention to provide a novel organizing system whereby individual work product or work pieces of a plurality of work products or workpieces can be identified with an associated user or owner after the work product or workpiece has been worked upon.

Another object of the present invention is to provide a novel means of identifying a workpiece and associating the identified workpiece with an owner or project so as to avoid loss of the workpiece or misidentification thereof.

Yet another object of the present invention is to provide a novel organizing system having a chart indicating owner or patient or project name and further identifying the characteristics of the project with further identification of the actual project by means of graphic sets of indicators which, through comparison of the project with the indicator, and with the owner or patient or project's name is associated therewith.

Still a further object is to provide a novel chart having indicia representative of names and product characteristics which includes indicators comparable with separate indicators on the actual workpiece identifying the workpiece.

BRIEF DESCRIPTION OF THE DRAWINGS

The features of the present invention which are believed to be novel are set forth with particularity in the appended claims. The present invention, both as to its organization and manner of operation, together with further objects and advantages thereof, may best be understood with reference to the following description, taken in connection with the accompanying drawings in which:

FIG. 1 is a perspective view of a work table and wall illustrating the novel organizer system of the present invention;

FIG. 2 is an enlarged view of the chart shown in FIG. 1 having a plurality of columns and rows;

FIG. 3 is a side elevational view of the chart shown in FIG. 2; and

FIG. 4 is a front elevational view of an indicator or identification label used on the workpiece for association with a similar indicator or label illustrated on the chart shown in FIG. 2.

DESCRIPTION OF THE PREFERRED EMBODIMENT

Referring to FIG. 1, the novel organizing system of the present invention is illustrated in the general direction of arrow 10 which includes a chart 11 that may be placed on a wall 12 for display-purposes or may be placed on the work surface of a table 13. The work surface 13 may support an eraser 14 as well as a compartmentized container 15 in which a plurality of indicators may be stored. Such an indicator is shown in FIG. 4 and is represented by numeral 16. The indicators 16 are affixed to a product or workpiece, such as a dental impression tray 17, and is represented by numeral 18. Additional indicators are also affixed to other dental impression trays which are represented by numerals 20 and 21 respectively.

The chart 11 is arranged with a plurality of columns, as indicated by numeral 22, and a plurality of rows, as indicated by numeral 23. A marker or pen 24 is removably carried on the chart 11 and may be used to place pertinent information or indicia in the spaces provided in the aforementioned rows and columns. A selected column, as indicated by numeral 25, includes a plurality of different indicator symbols which are correlated with the indicators 16 so that when an indicator is placed on the work product, such as indicator 18 on dental impression tray 17, a particular row 23 may be associated therewith and the information or indicia carried on that row would be pertinent solely for that work product. The top row of the plurality of rows includes nomenclature for the respective columns. The first column starting from the left hand side, as shown in FIG. 2, is for graphic representations of the indicators. The indicators may be of a specialized shape or configuration and there is no limit to the geometric representations which can be employed. Alternately, other indicators may be employed which represent graphic representations, such as figures or other characters, and colors are also contemplated in addition to the variety of shapes. In the present illustration, both shape and color representations are employed. The second column is expanded and is used for patient or product name. When the organizing system is used in the medical field, patient's name may be placed in this column, or if an owner of a product is involved, the owner's name may be placed in the respective spaces in the second column. The remainder of the columns extending to the right hand side may be numbered as illustrated, and may include indicia pertaining to the type of kind of work being performed for the patient or on the product listed. The present invention is not limited to any particular indicia, only to the spaces provided for delineating the indicia. The separate indicator 16, as shown in FIG. 4, corresponds to shape of the graphic indicator shown in the first column on the chart; however, it is to be understood that each of the rows includes a different color for each of the indicators shown on the chart and that a plurality of different colored separate indicators 16 are carried in the various compartments of the container 15 and are available for removal from the compartments. Once a particular color of indicator 16 has been removed from the container, it is placed in the impression material carried on a selected one of the trays 17, 20 or 21. The indicator 16 is not merely pressed or adhesively attached to the product or tray but is actually or preferably embedded into the work product itself, such as the impression material. Therefore, when the impression material is set, the indicator 16 will be securely and fixedly attached thereto. The indicator 16 will not interfere with further processing of the dental impression or other work that needs to be performed on the product.

In FIGS. 2 and 3, it can be seen that the organizer system of the present invention further includes a marking implement 24 which is removably carried on a holder 26 carried on the board or chart 11. Preferably, the holder is secured to the edge marginal region of the chart and the marking implement 24 is removably carried on the holder by means of a hook and pile fastener 27. The marking implement 24 may be used to apply the patient or product nomenclature within the second column of the chart and can be used to check or mark other available squares indicating work performed on the patients or products workpiece. The eraser 14 may be employed for removing such indicia or nomenclature when no longer needed.

Therefore, it can be seen that the inventive organizing system of the present invention provides a novel means for keeping track of a work product and for identifying the product with a particular patient or project.

In actual use, in connection with a dental practice, a patient's name is placed in the second column of the chart adjacent to a particular indicator 23. The indicator is of a special shape and identifying color so as not to be confused with other indicators on the same chart. Next, the work performed on the dental product is checked in available crossing rows and columns utilizing the marking pen 24. Simultaneously, a separate indicator 16 of the same color or identifying characteristic as that associated with the patient's name by indicator 23 on the chart is physically attached to the product, such as product 17, and represented by indicator 18. Now, all products can be moved about the work surface and can be worked upon by the laboratory without confusion or misidentification. When it is time to return the impression or other work product with respect to the associated patient, the color of the locator 16 (18) is compared with the coloar of the indicator 23 on the chart. After comparison, identification is assured. The different colors of the indicators, whether on the chart or separate, may be chosen from standard colors, such as red, green, blue or yellow, etc.

While particular embodiments of the present invention have been shown and described, it will be obvious to those skilled in the art that changes and modifications may be made without departing from this invention in its broader aspects and, therefore, the aim in the appended claims is to cover all such changes and modifications as fall within the true spirit and scope of this invention.

What is claimed is:

1. In an organizer system for identifying a work product with a particular patient or project, the combination comprising:

a work product;

a chart having a plurality of vertical columns and horizontal rows overlapping each other to define a plurality of squares;

said chart having a markable surface for removably accepting indicia in respective ones of said squares representing said patient or project and work performed therefor or thereon;

indicator means carried on said chart adjacent to said patient or project indicia identifying said patient or project; and said indicator means further including a plurality of individual indicators separate from said indicator means carried on said chart and selected ones of said individual indicators embedded in said work product matching said indicator means carried on said chart associated with said patient or project identifying indicia.

2. The invention as defined in claim 1 wherein:

said indicator means comprises a first set of indicators carried on said chart surface and a second set of indicators separate from said first set and characterized as a plurality of individual indicators;

selected ones of said first set and said second set of indicators constituting identical pairs for comparison in determining identification of said patient or project.

3. The invention as defined in claim 2 wherein:

each pair of said indicators in said indicator means is different from other ones of said pairs by color.

4. The invention as defined in claim 3 wherein:

each indicator is characterized by a distinctive shape.

5. The invention as defined by claim 4 including:

a marking implement; and attachment means for removably securing said marking implement to said chart; and an eraser associated with said chart for removing said indicia.

* * * * *